US008876870B2

(12) United States Patent
Qureshi (10) Patent No.: US 8,876,870 B2
(45) Date of Patent: Nov. 4, 2014

(54) INTRASPINAL DEVICE DEPLOYED THROUGH PERCUTANEOUS APPROACH INTO SUBARACHNOID OR INTRADURAL SPACE OF VERTEBRAL CANAL TO PROTECT SPINAL CORD FROM EXTERNAL COMPRESSION

(76) Inventor: Adnan Iqbal Qureshi, Edina, MN (US)

( * ) Notice: Subject to any disclaimer, the term of this patent is extended or adjusted under 35 U.S.C. 154(b) by 829 days.

(21) Appl. No.: 12/768,423

(22) Filed: Apr. 27, 2010

(65) Prior Publication Data
US 2011/0264217 A1 Oct. 27, 2011

(51) Int. Cl.
*A61B 17/88* (2006.01)
*A61B 17/70* (2006.01)
*A61F 2/44* (2006.01)
*A61F 2/30* (2006.01)

(52) U.S. Cl.
CPC ......... *A61B 17/7061* (2013.01); *A61B 17/8858* (2013.01); *A61F 2002/4435* (2013.01); *A61F 2002/3008* (2013.01); *A61F 2002/30581* (2013.01); *A61F 2210/0014* (2013.01); *A61F 2310/00023* (2013.01)
USPC ........................................ 606/279; 606/86 A (58) Field of Classification Search
USPC ............ 600/37; 606/60, 246, 279, 86 A, 914, 606/299, 911, 78, 192, 63, 68; 623/17.11; 607/117
See application file for complete search history.

(56) References Cited

U.S. PATENT DOCUMENTS

| | | | |
|---|---|---|---|
| 4,402,319 A | 9/1983 | Handa et al. | |
| 4,772,287 A | 9/1988 | Ray et al. | |
| 6,264,695 B1 | 7/2001 | Stoy | |
| 6,375,668 B1 | 4/2002 | Gifford et al. | |
| 7,011,647 B2 | 3/2006 | Purdy et al. | |
| 7,306,598 B2 | 12/2007 | Truckai et al. | |
| 7,455,666 B2 | 11/2008 | Purdy | |
| 7,520,888 B2 | 4/2009 | Trieu | |
| 2002/0123750 A1 | 9/2002 | Eisermann et al. | |
| 2002/0169473 A1 | 11/2002 | Sepetka et al. | |
| 2003/0130577 A1 | 7/2003 | Purdy et al. | |
| 2005/0137612 A1* | 6/2005 | Assell et al. | 606/108 |
| 2005/0267527 A1 | 12/2005 | Sandoval et al. | |
| 2006/0036259 A1 | 2/2006 | Carl et al. | |
| 2006/0259110 A1* | 11/2006 | Wallace et al. | 607/117 |
| 2007/0005041 A1* | 1/2007 | Frassica et al. | 604/544 |
| 2007/0161991 A1* | 7/2007 | Altarac et al. | 606/61 |
| 2007/0179426 A1 | 8/2007 | Selden | |
| 2007/0179599 A1* | 8/2007 | Brodbeck et al. | 623/1.44 |
| 2007/0213717 A1* | 9/2007 | Trieu et al. | 606/61 |
| 2008/0188916 A1* | 8/2008 | Jones et al. | 607/116 |
| 2009/0292315 A1* | 11/2009 | Trieu | 606/249 |

FOREIGN PATENT DOCUMENTS

WO 9947082 A1 9/1999

* cited by examiner

*Primary Examiner* — David Bates
*Assistant Examiner* — Samuel Hanna
(74) *Attorney, Agent, or Firm* — Nikolai & Mersereau, P.A.; C. G. Mersereau (57) ABSTRACT

To shield the spinal cord from an external compression, a barrier device having a self-expanding frame and covered with a non-porous elastomeric sheet is routed through either the subarachnoid or intradural space to the site of the compression through the lumen of a delivery catheter that is percutaneously inserted using an introducer needle. When the distal end of the delivery catheter is proximate the site of the compression, the barrier device is pushed out the distal end of the catheter and allowed to self-expand so as to be interposed between the compression and the spinal cord to prevent impingement.

12 Claims, 11 Drawing Sheets

INTRASPINAL DEVICE DEPLOYED THROUGH PERCUTANEOUS APPROACH INTO SUBARACHNOID OR INTRADURAL SPACE OF VERTEBRAL CANAL TO PROTECT SPINAL CORD FROM EXTERNAL COMPRESSION

I. FIELD OF INVENTION

The present invention relates to a medical device deployed through a minimally invasive procedure to protect the spinal cord from external compression.

II. BACKGROUND OF INVENTION

External compression of spinal cord through variety of sources including retrograde movement of a vertebral body or disc, a tumor, or a vascular malformation remains major causes of myelopathy. The external compression of the spinal cord leads to paraparesis, segmental sensory loss, and sometimes urinary and fecal incontinence.

In humans, the vertebral column is a column usually consisting of 33 vertebrae, the sacrum, intervertebral discs, and the coccyx situated in the dorsal aspect of the torso. The vertebral canal follows the different curves of the spinal column. It is large and triangular in those parts of the column which enjoy the greatest freedom of movement, such as the cervical and lumbar regions and is small and rounded in the thoracic region, where motion is more limited. The spinal cord is located inside the vertebral canal and extends from the foramen magnum down to the level of the first and second lumbar vertebrae (at birth, down to second and third lumbar vertebrae). The spinal cord is composed of 31 segments: 8 cervical (C), 12 thoracic (T), 5 lumbar (L), 5 sacral (S), and 1 coccygeal (Co), mainly vestigial. The spinal nerves comprise the sensory nerve roots, which enter the spinal cord at each level, and the motor roots, which emerge from the cord at each level, which is formed by the foramina of 7 cervical, 12 thoracic, 5 lumbar, and 5 sacral vertebrae, which together form the spine. The conus medullaris is the cone-shaped termination of the caudal cord. The pia mater continues caudally as the filum terminale through the dural sac and attaches to the coccyx. The coccyx has only one spinal segment. Several macroscopic grooves are discernible on the surface of the spinal cord. Most prominent is the anterior median fissure, which is occupied by the anterior spinal artery. The posterior median sulcus is less prominent. The anterior and posterior nerve rootlets emerge at the anterolateral and posterolateral sulci.

Within the vertebral canal, both spinal cord (CNS) and spinal roots (PNS) are enveloped by meninges. Spinal dura mater is separated from periosteum lining the vertebral canal by an epidural space that contains a variable amount of fat (in the cranial cavity, dura mater and periosteum merge so an epidural space does not exist). Three layers of meninges envelop the spinal cord and the roots of spinal nerves. The most superficial menix is dura mater. It is protective by virtue of its high collagen content. Arachnoid (arachnoid membrane) is thin and delicate, being composed of flattened fibrocytes and flimsy strands of collagen. In life, arachnoid contacts dura mater due to cerebrospinal fluid pressure within the subarachnoid space. Arachnoid trabeculae are delicate strands of arachnoid that traverse the subarachnoid space to join pia mater. The subarachnoid space filled with cerebrospinal fluid forms a space where devices can be advanced and deployed between the vertebral, disc, and external compression and spinal cord itself. Pia mater consists of flattened fibrocytes that line the subarachnoid space and collagen bundles in contact with glial cells at the surface of the spinal cord and spinal roots. Bilaterally, pia mater collagen is thickened to form denticulate ligaments. Processes of the ligaments periodically join dura mater and thus, within dura mater, the spinal cord is suspended by bilateral denticulate ligaments and thereby surrounded by protective cerebrospinal fluid within the subarachnoid space.

Spinal cord compression develops when the spinal cord is compressed by bone fragments from a vertebral fracture, a tumor, abscess, ruptured intervertebral disc or other lesion. It is regarded as a medical emergency independent of its cause, and requires swift diagnosis and treatment to prevent long-term disability due to irreversible spinal cord injury. Surgery is indicated in localized compression with or without postoperative radiation is delivered within 2-3 weeks of surgical decompression. Surgery usually comprises of a laminectomy to relieve pressure on the spinal cord or the nerve roots. The lamina is the bony roof of the spinal canal. Laminectomy is the term used to refer to the process of removing the lamina (usually both sides). Removing the lamina increases the size of the spinal canal, giving more room for the spinal cord or nerve roots. However, the process is extensive and is associated with complications such as bleeding within the operative sites, or worsening of neurological deficits.

SUMMARY OF THE INVENTION

The present invention meets the above-described need by providing a method to deploy a self expanding device around the spinal cord using a small microcatheter through a percutaneous needle puncture at lumbar interspace from posterior approach. The process is similar to a lumbar puncture and introduction of a lumbar drain. However, a flexible introducer sheath is advanced through a percutaneous needle under fluoroscopic guidance towards the cephalic direction. A microcatheter is then advanced through the sheath and under fluoroscopic guidance through the anterior space between spinal cord and vertebral bodies and discs. The selected microcatheter could be advanced over a 0.014-inch microguidewire and navigated to the site of compression. A device comprised on a substantially flat, but slightly rounded dumbbell-shaped structure that is comprised of meshwork of Nitinol, and porous membrane. The device is introduced in a compressed manner through the microcatheter. The device is pushed through the microcatheter by a microwire until it reaches the distal end of the microcatheter. The microcatheter is withdrawn once the device reaches the distal end of the microcatheter. The device is unsheathed by the withdrawal of the microcatheter and self expansile properties of the device. The device is deployed between the spinal cord and vertebral bodies and disc. The device is aligned so the long axis is parallel to the axis of the spinal cord and provides a protective barrier in front of the spinal cord.

BRIEF DESCRIPTION OF THE DRAWINGS

The foregoing features, objects and advantages of the invention will become apparent to those skilled in the art from the following detailed description of a preferred embodiment, especially when considered in conjunction with the accompanying drawings in which.

DESCRIPTION OF THE PREFERRED EMBODIMENT

Figure 1:
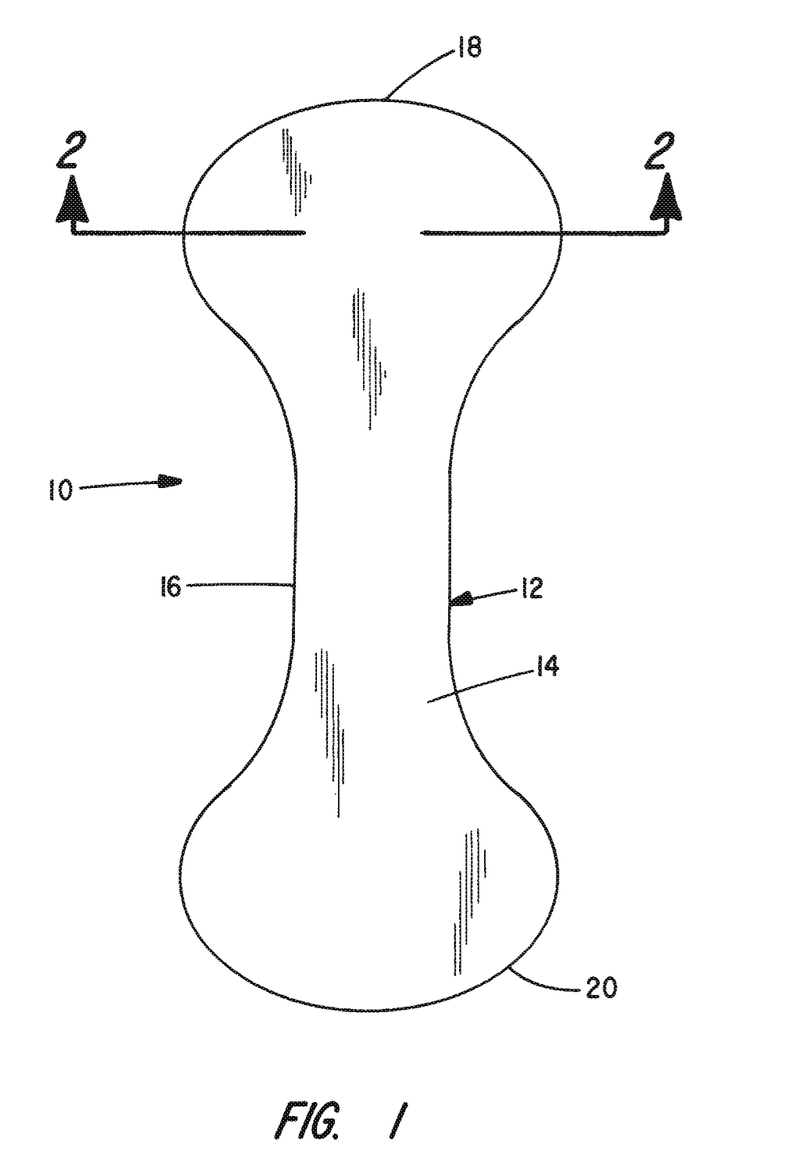
FIG. 1 is an antereo-posterior view of the self-expanding, dumbbell-shaped, barrier device in its expanded form.

Referring to FIG. 1, the present invention comprises a self-expanding, generally flat, dumbbell-shaped, implantable barrier device 10 which can be introduced in a compressed form through a flexible delivery tube into the subarachnoid or intradural spaces within the vertebral canal under fluoroscopic guidance. The implantable barrier device includes a frame 12 formed from a material exhibiting shape memory properties and consisting of a closed loop of wire where the frame is enclosed within a covering 14 of a selected non-porous membrane material. Without limitation, the frame 12 may be formed from one or more strands of Nitinol wire with plural strands being wound as a cable. The non-porous membrane covering 14 for the frame may be polyurethane, latex or another synthetic material that is somewhat flexible so as to be capable of being readily rolled or folded and which is otherwise body-compatible.

FIG. 1 shows the implantable barrier device 10 in its fully expanded state and the dumbbell shape includes a central rectilinear segment 16 on opposed ends of which are formed somewhat circular lobes 18, 20.

As will be explained in greater detail herein below, the rounded lobes 18, 20 coact with spongy tissue of the subarachnoid or intradural space consisting of delicate connective tissue filaments termed trabeculae to hold the barrier device 10 in place within a patient's spinal canal. If the frame 12 is formed of a Nitinol wire, it will be radio-opaque for visualization under fluoroscopy. However, if a plastic strand of a shape memory material is employed as the frame, radio-opaque markers should be added to it to facilitate placement.

Figure 2:
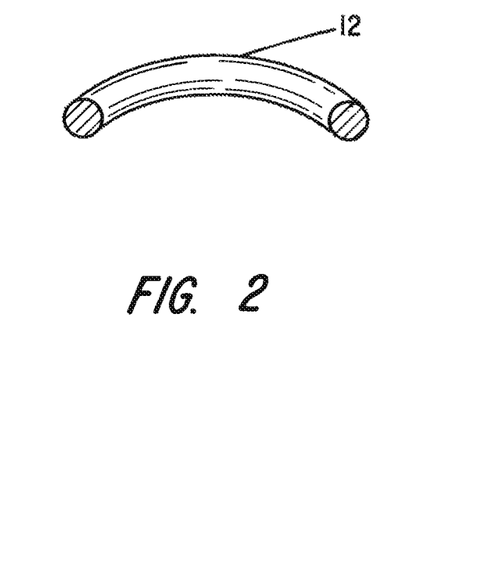
FIG. 2 is cross-section view of the self-expanding, dumbbell-shaped, barrier device taken along the line 2-2 in FIG. 1.

Referring to the cross-sectional view of FIG. 2, it can be seen that the frame is slightly convex and not perfectly flat. Thus, when placed within the spinal canal at a desired target location proximate an external compression of the spinal cord, the concave surface of the barrier device 10 will help separate the defect causing the external compression from engagement with the spinal cord. That is to say, the inner and outer layers of the non-porous membrane fabric enclosing the frame 12 serve to maintain a separation or barrier between the external compression point and the adjacent spinal cord nerves.

Figure 3:
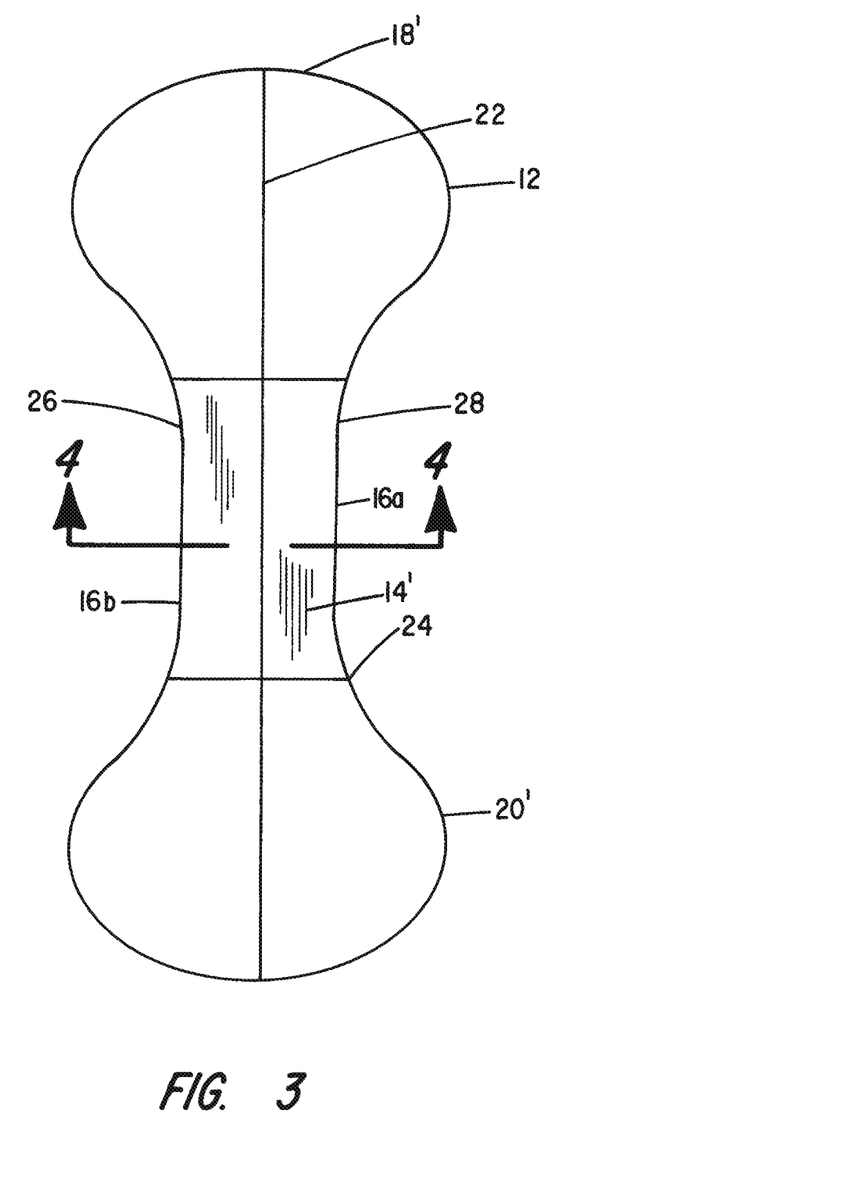
FIG. 3 is an antereo-posterior view of an alternative embodiment of the self-expanding, dumbbell-shaped, barrier device in its expanded form.
Figure 4:
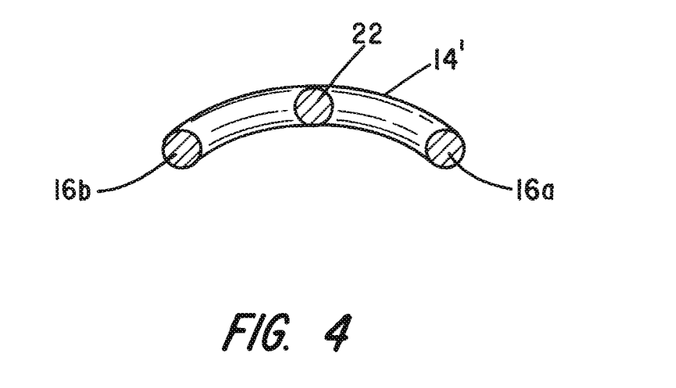
FIG. 4 is a cross-section view taken along the line 4-4 in FIG. 3.

In the embodiment of FIG. 3, the non-porous membrane 14' only partially surrounds the frame 12 over the rectilinear portion of the dumbbell and the rounded end lobes 18', 20' are left uncovered. A centrally disposed, longitudinally extending strand of Nitinol wire 22 connects the upper and lower ends of the dumbbell-shaped implantable barrier device 10 together within the center of the device for axial support. Here, the porous membrane 14' is wrapped around the two, spaced-apart linear frame segments 16a and 16b and may be attached to the frame at the four corner points, as at 24, using a suitable adhesive. Again with regard to FIG. 4, the two parallel segments 26, 28 of the dumbbell-shaped structure are curved with a concave aspect which, when placed in the spinal canal will be facing the vertebral bodies to better insure successful fixation at the target location. The unique dumbbell configuration is specifically designed to insure successful fixation following deployment from a delivery catheter next to be described.

Figure 5:
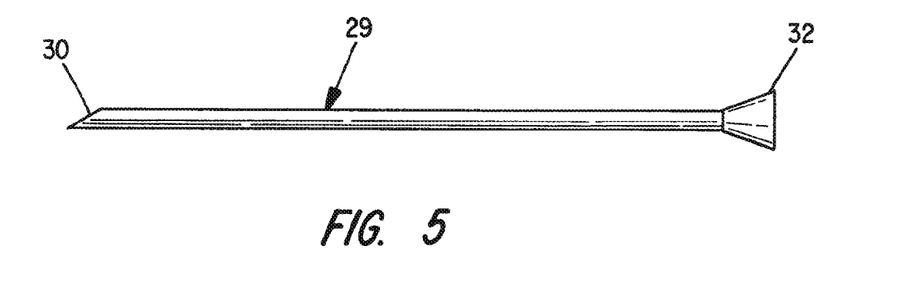
FIG. 5 is a longitudinal view of a 16 gauge needle used for standard lumbar drain placement.

Referring now to FIG. 5, there is shown an introducer needle 29 which, for the present application, could be a 16 gauge needle having a sharpened and beveled distal end 30 and a flared or funnel-shaped proximal end 32 for ease in handling and maneuvering.

Figure 6:
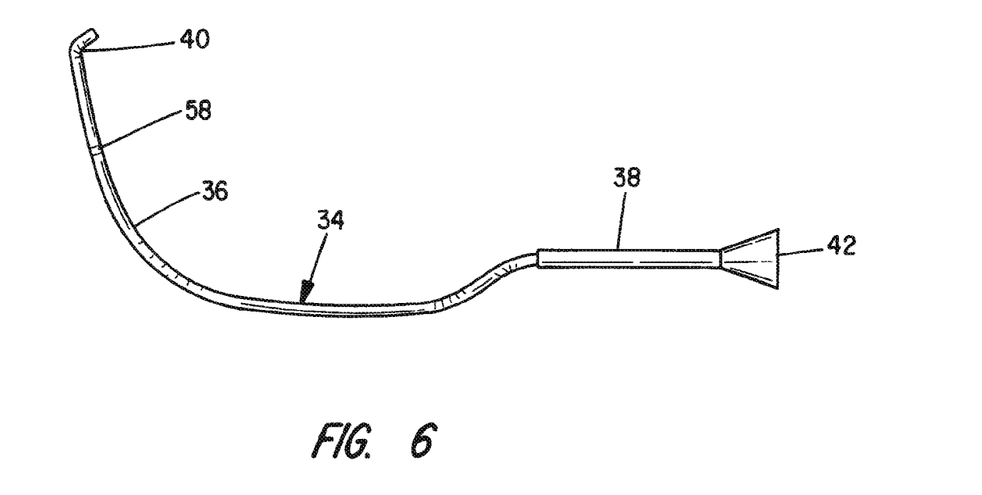
FIG. 6 is a longitudinal view of a flexible plastic delivery catheter that is comprised of a distal flexible component and a proximal stiff component.
Figure 7:
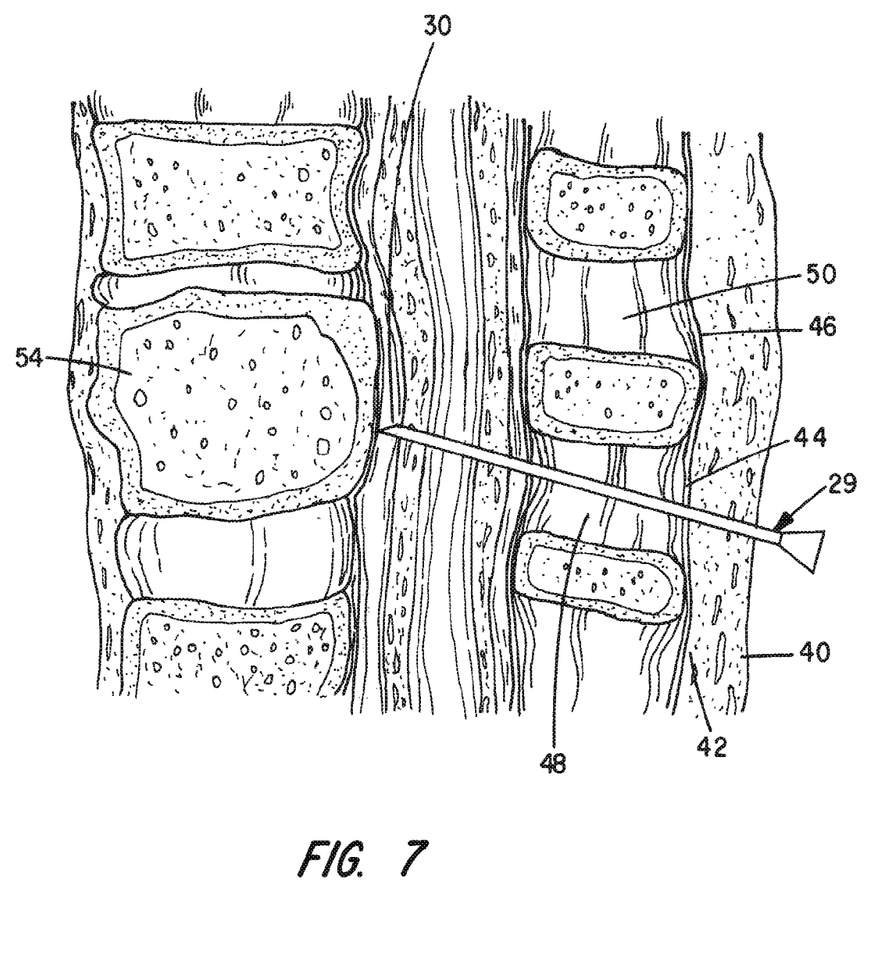
FIG. 7 illustrates the percutaneous introduction of the needle of FIG. 5 into the subarachnoid space through the skin, soft tissue, ligametum favum via the $2^{nd}$, $3^{rd}$ or $4^{th}$ intervertebral space in a saggital view.

FIG. 6 is a longitudinal view of a flexible plastic tube 34, referred to herein as a delivery catheter that is comprised of a distal flexible component 36 and a somewhat stiffer proximal component 38. The distal flexible component 36 may, for example, be in a range of from 16 to 26 cms with the length to be chosen depending upon distance measurements acquired from either CT or MRI scans. The flexible end portion 36 may have a short bent portion 40 at its distal end to facilitate navigation through the subarachnoid or intradural space of the vertebral canal by manipulation of the delivery tube's external proximal end 42. The flexible portion 36 of the delivery tube allows it to adjust to the curves within the subarachnoid or intradural space along the length of the vertebral canal to be traversed. The proximal stiff end portion 38 of the delivery catheter is relatively short and may range between 5 and 10 cms. This stiff end provides support and prevents collapse in the segment of the delivery catheter 34 that will be resident within the skin 40, soft tissue 42, intervertebral space 44, the supraspinous ligament 46, the interspinous ligament 48 and the ligamentum flavum 50 shown in the saggital view of FIG. 7 which has been included herein to illustrate the trajectory of the needle 29 placement through the intervertebral foramen. The needle also penetrates through dura mater to enter the subarachnoid or intradural space. The bevel 30 of the needle faces cephalad to insure that passage of the delivery catheter 34 will be in the cephalad direction.

Figure 8:
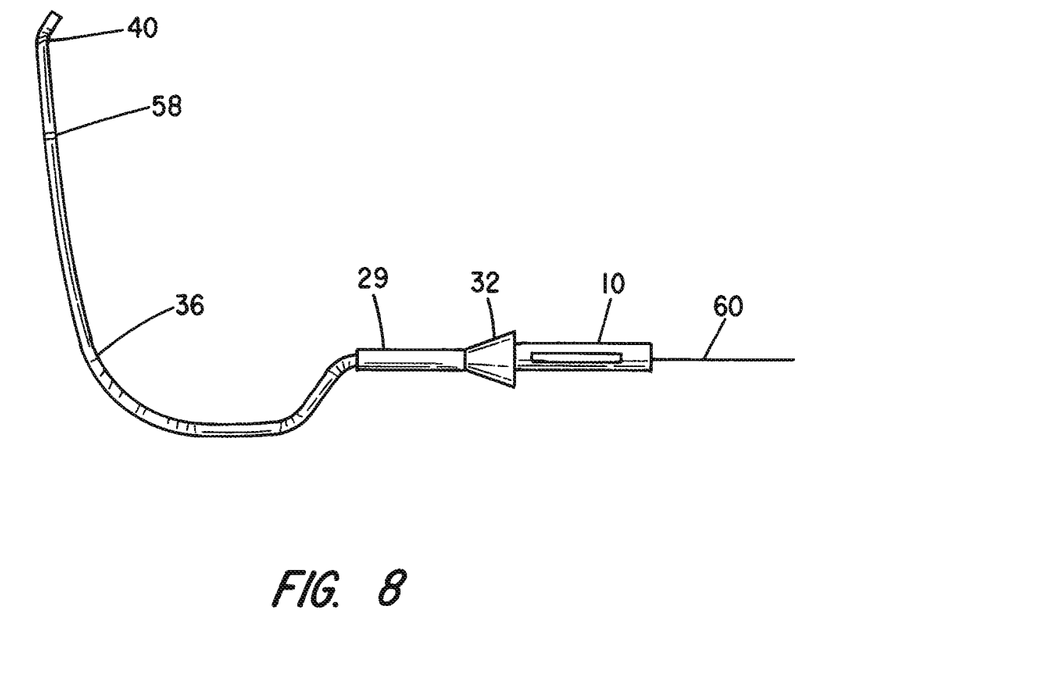
FIG. 8 illustrates the introduction of the delivery catheter of FIG. 6 and the barrier device of FIG. 1 or 3 through the introducer needle in a longitudinal view, also identifying the radio-opaque markers at a distal end of the delivery catheter.

FIG. 8 shows the insertion of the implantable barrier device 10 in its compressed state into the proximal end of the delivery catheter. From there, it is pushed through the lumen of the delivery catheter using a pusher wire 60 that is sufficiently flexible to allow its advancement through the curves of the delivery catheter. Again, the distal end of the pusher is made to be radio-opaque to allow visualization of the pusher movements within the delivery catheter.

Figure 9:
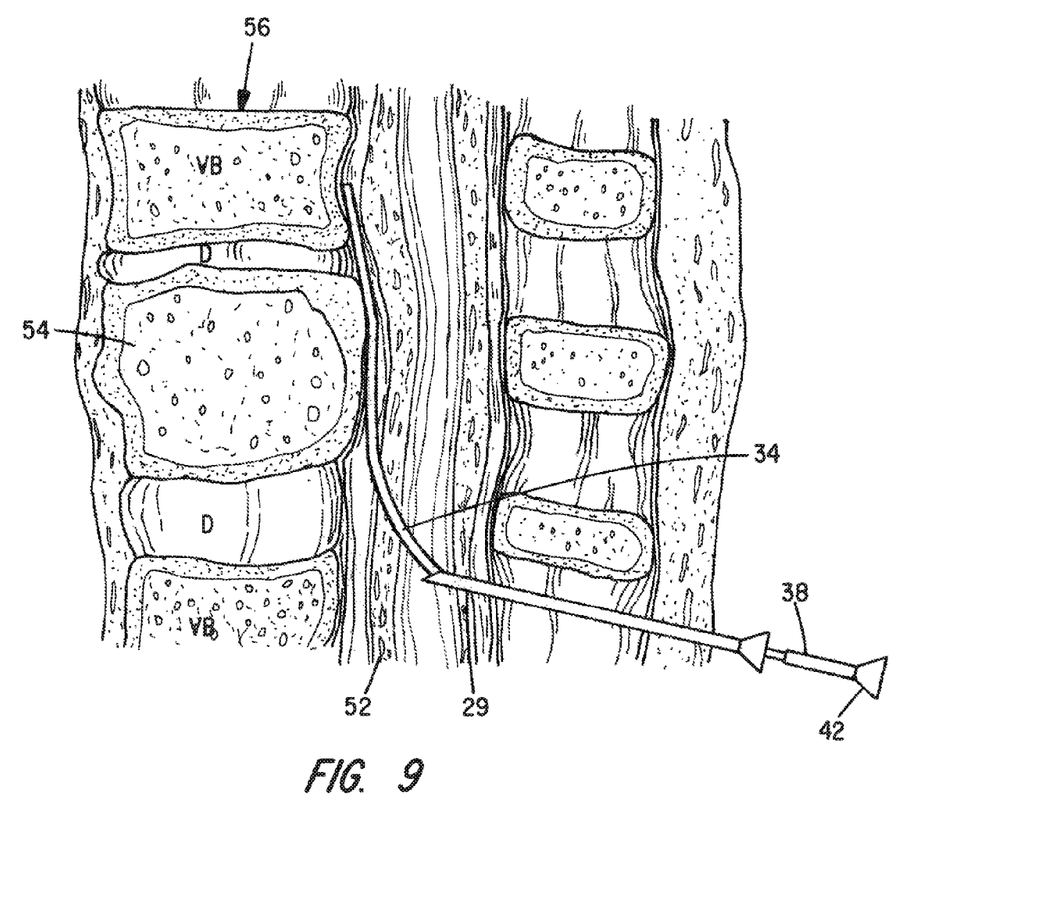
FIG. 9 is a saggital view demonstrating the advancement of the delivery catheter through the subarachnoid space in the anterior compartment between the external compressive lesion and the spinal cord.

Referring next to FIG. 9, it shows the introducer needle 29 inserted into the subarachnoid space 52 and with the delivery catheter or tube 34 being fed through the introducer needle and across the site of compression at 54. As those skilled in the art appreciate, the use of the introducer needle facilitates passage of the flexible delivery catheter through the skin, soft tissue, intervertebral space, supraspinous ligament, intraspinous ligament and ligamentum flavum and into the subarachnoid or intradural space 52. The delivery tube 34 can be navigated and advanced through the vertebral canal by manipulation at the external proximal end 42 thereof.

Ideally, the delivery tube is placed between the spinal cord and vertebral column 56 within the subarachnoid or intradural space 52 and the distal end extends past the anterior compartment of the vertebral canal between the vertebral bodies VB, disks D and external compressive lesion 54 and spinal cord.

If additional support is necessary for advancing and navigating the delivery tube within the subarachnoid or intradural space, this support can be provided by the temporary introduction of a flexible guidewire (not shown) through the delivery tube as is known in the art.

It has been found expedient to include a radio-opaque marker at the distal end 40 of the delivery tube 34 to allow for continuous visualization of movement and placement of the tube under fluoroscopic guidance. It is also contemplated that a contrast media may be injected for better fluoroscopic visualization of the subarachnoid space whereby the relationship between the distal end of the delivery catheter and compressive lesion 54 is enhanced. A second radio-opaque marker 58 (FIG. 6) may be placed approximately 5 cms proximal to the distal end 40 of the delivery catheter. This second marker will allow detection of a pushing tool crossing a point after which the self-expanding, dumbbell-shaped barrier device 10 will be ejected out of the delivery catheter with further advancement of the pusher.

Figure 10:
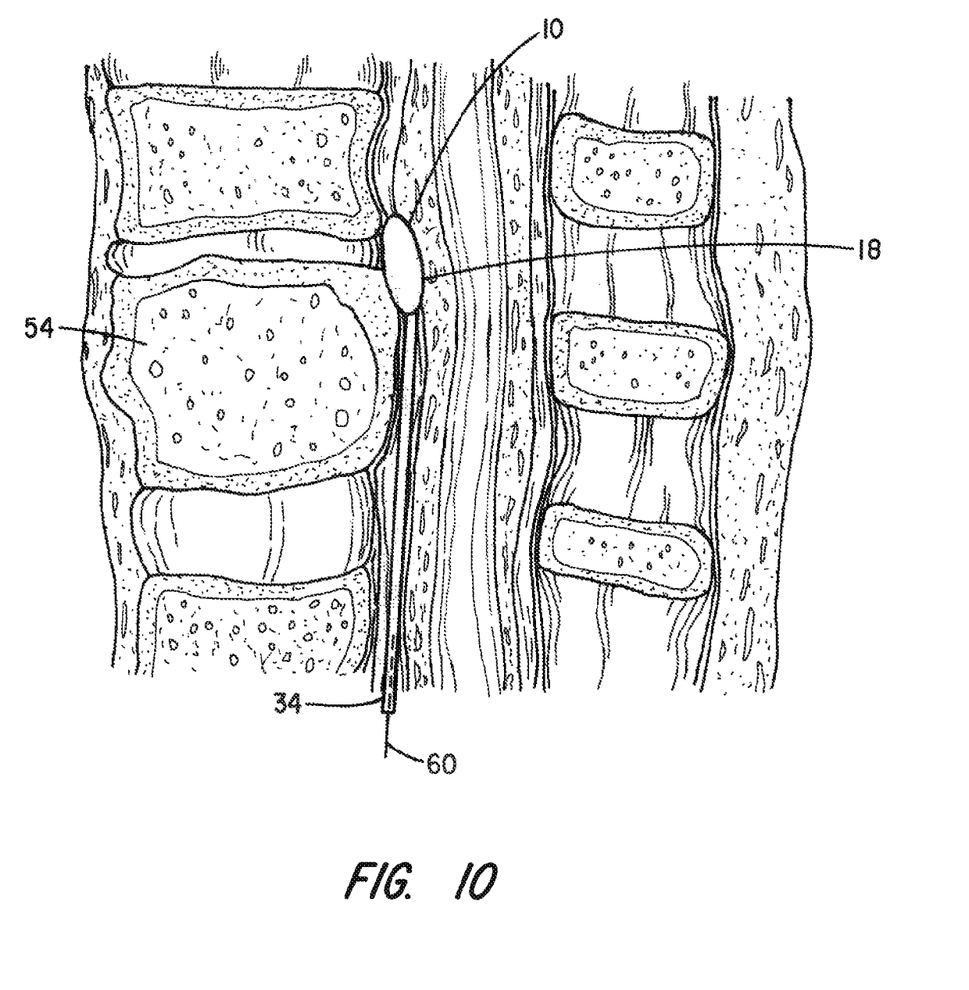
FIG. 10 is a longitudinal view illustrating the advancement of the barrier device of FIG. 1 in its compressed form through the central lumen of the delivery catheter.
Figure 11:
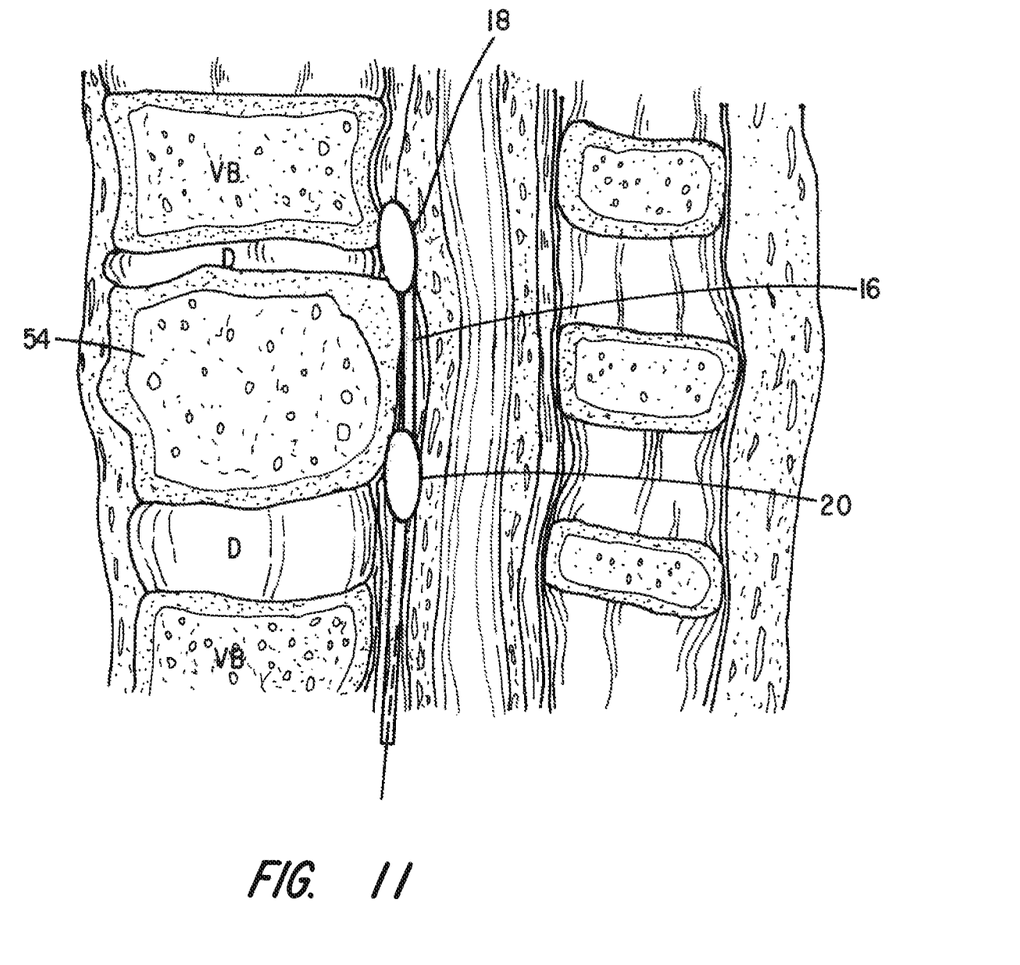
FIG. 11 is an enlarged lateral view demonstrating the expansion of the barrier device of FIG. 1 within the subarachnoid space upon the withdrawal of the delivery catheter while holding the pusher stationary.
Figure 12:
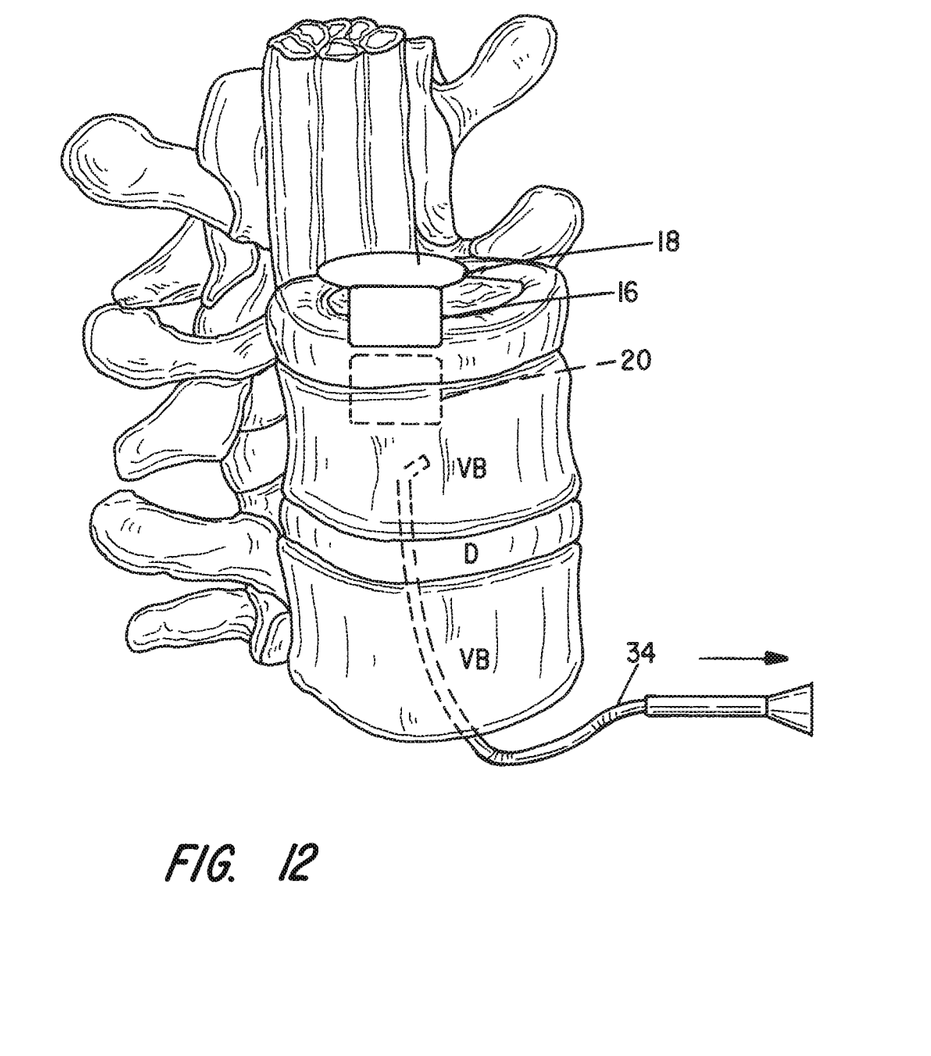
FIG. 12 is an enlarged anterior view illustrating the dumbbell-shaped barrier device after complete expansion within the subarachnoid space following withdrawal of the delivery catheter.

To deploy the implantable barrier device, once the distal opaque marker of the pusher and the proximal marker 58 on the delivery catheter overlap, the delivery catheter is slowly withdrawn in the proximal direction while holding the pusher wire 60 stationary. As the delivery catheter uncovers the implant device 10 as seen in FIG. 10, it self-expands to its dumbbell shape within the subarachnoid or intradural space in a stepwise manner. First, the distalmost rounded end 18 will self-expand, followed by unfurling of the rectilinear central section 16 and finally the proximal founded end portion 20. The flaring of both rounded ends and the concave shape facing the vertebral body, disk and external compression as seen in FIGS. 11 and 12 insure successful fixation in the location of the deployment. The delivery catheter is now removed.

Figure 13:
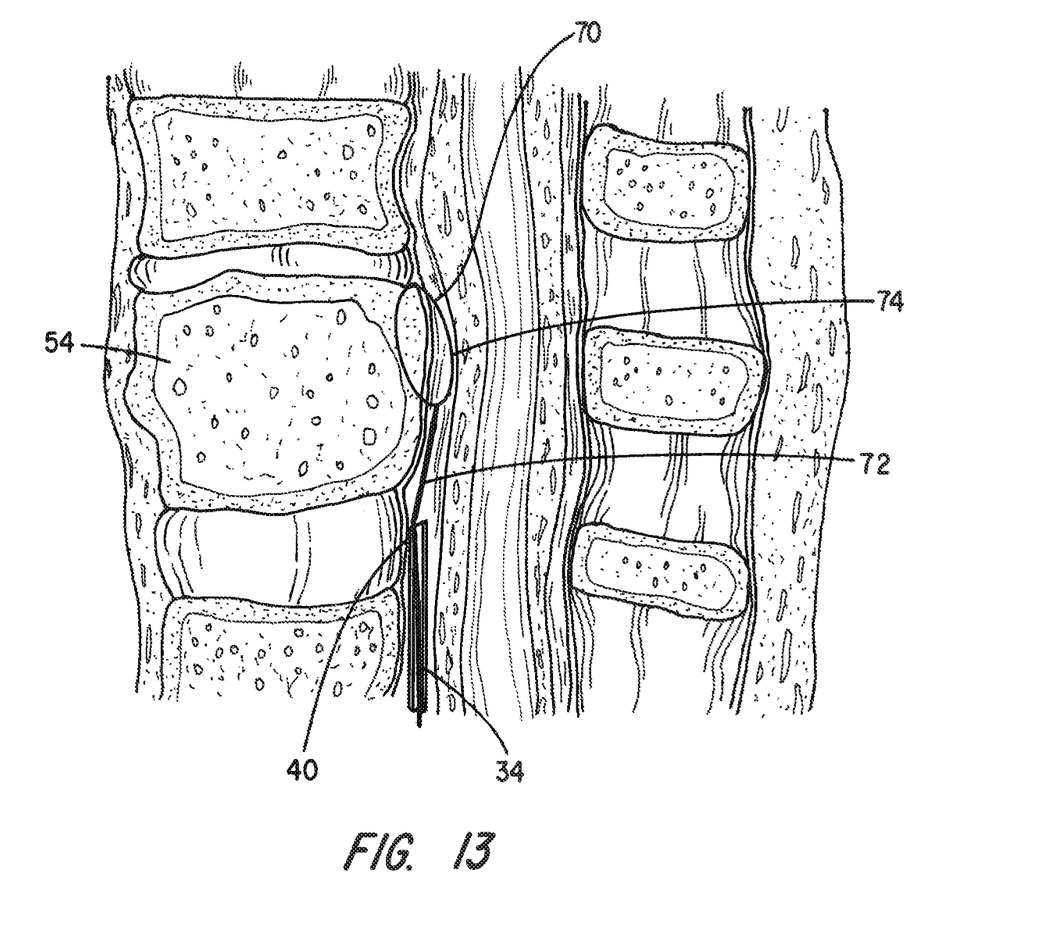
FIG. 13 illustrates the use of a fragmentation tool having its loop deployed across a protubering portion of a lesion.

In the event a compressive lesion does not allow cephalad progress of the delivery catheter across the lesion, a further step may be employed to rectify this situation. Specifically, the delivery catheter can be placed with its distal end slightly proximal to the lesion as shown in FIG. 13. Then, a wire snare 70 can be used to fragment the lesion. In FIG. 13, the snare comprises an elongated pull wire 72 preferably made of Nitinol whose proximal end extends exteriorly to the proximal end of the delivery catheter 34 and having a loop 74 at its distal end can be advanced through the delivery catheter 34 and upon exit of the loop from the confines of the delivery catheter, it opens up, allowing the loop to be placed about the lesion to be fragmented. Next, the delivery catheter 34 is advanced in the distal direction while the pull wire 72 is held stationary. This has the effect of closing the loop about the lesion and ultimately excising a fragment. The closing loop acts as a garrote, cutting through the protuberant portion and releasing the fragment in the subarachnoid or intradural space. The fragmentation device is then retracted from the delivery catheter and suction may be applied to the external proximal end thereof using an empty syringe for creating a vacuum as its plunger is retracted. The process of aspiration at the distal end of the delivery catheter functions to remove the severed fragment of the compression lesion from the subarachnoid space. This process can be repeated several times until enough lesion portions have been removed to allow passage of the delivery catheter across the lesion. Thus, a minimally invasive procedure is provided that allows debulking of a compressive lesion within the subarachnoid space surrounding the spinal cord under fluoroscopic guidance several levels high up to the thoracic and cervical levels from a percutaneous insertion at an intervertebral space in the lumbar region.

It can be seen that the present invention provides a minimally invasive method for implanting a barrier device in the subarachnoid or intradural space of the spinal column in surrounding relation to the spinal cord whereby the effects of external compressions on the spinal cord can be addressed to thereby alleviate pain. The delivery catheter can be inserted in the lumbar region and advanced cephalically to the thoracic and cervical levels via the subarachnoid space or via the intradural layer.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. A method for treating effects of external compressions of a spinal cord at a site in a spinal column comprising the steps of:
   (a) providing an implantable barrier device for treating effects of the external compression of the spinal cord comprising:
   I) a frame member formed from a material exhibiting shape memory properties, said frame when unconstrained, having a generally rectangular center section with a width dimension less than a length dimension and flat, rounded end portions having a diameter of greater dimension than said width dimension, the frame member forming the general shape of a dumbbell, being generally symmetrical about a central longitudinal axis and having a convex contour centered about the central longitudinal axis; and
   2) a non-porous elastomeric sheet applied to the frame member such that the sheet is held taut by the frame member when the frame member is not being constrained;
   (b) percutaneously inserting a tubular needle into a patient at a location beneath the location of the external spinal cord compression site, such that the needle tip resides in a subarachnoid or intradural space in the spinal column;
   (c) advancing a delivery catheter through the tubular needle and continuing to advance the delivery catheter cephalically under imaging guidance until a distal end of the delivery catheter extends cephalically beyond the location of the external compression site;

(d) inserting the barrier device in a compressed state into a proximal end of a lumen of the delivery catheter;

(e) pushing the barrier device through said lumen with a pushing tool until the barrier device reaches the distal end of the delivery catheter; and (f) withdrawing the delivery catheter in a proximal direction while holding the pushing tool stationary to thereby cause the barrier device to be released from the delivery catheter in, stages and self-expand in a manner such that the barrier device is placed between, and provides a structural barrier separating adjacent spinal cord nerves and the external compression at the external compression site;

(g) prior to step (d) performing the steps of:

(1) advancing a wire of a shape memory material having a loop at a distal end thereof through the lumen of the delivery catheter;

(2) extending the loop beyond the distal end of the delivery catheter and about a protuberance on a posterior surface of a vertebral body; and (3) advancing the distal end of the delivery catheter cephalically while holding the wire stationary to thereby close the loop about the protuberance to sever the protuberance.

2. The method of claim 1 and including a further step of aspirating the severed protuberance through the lumen of the delivery catheter.

3. A method for treating effects of external compressions of a spinal cord at a site in a spinal column comprising the steps of:

(a) providing an implantable barrier device for treating effects of the external compression of the spinal cord comprising:

I) a frame member formed from a material exhibiting shape memory properties, said frame when unconstrained, having a generally rectangular center section with a width dimension less than a length dimension and flat, rounded end portions having a diameter of greater dimension than said width dimension, the frame member forming the general shape of a dumbbell, being generally symmetrical about a central longitudinal axis and having a convex contour centered about the central longitudinal axis; and 2) a non-porous elastomeric sheet applied to the frame member such that the sheet is held taut by the frame member when the frame member is not being constrained;

3) wherein only the rectangular center section of the frame is covered by the elastomeric sheet;

(b) percutaneously inserting a tubular needle into a patient at a location beneath the location of the external spinal cord compression site, such that the needle tip resides in a subarachnoid or intradural space in the spinal column;

(c) advancing a delivery catheter through the tubular needle and continuing to advance the delivery catheter cephalically under imaging guidance until a distal end of the delivery catheter extends cephalically beyond the location of the external compression site;

(d) inserting the barrier device in a compressed state into a proximal end of a lumen of the delivery catheter;

(e) pushing the barrier device through said lumen with a pushing tool until the barrier device reaches the distal end of the delivery catheter; and (f) withdrawing the delivery catheter in a proximal direction while holding the pushing tool stationary to thereby cause the barrier device to be released from the delivery catheter in, stages and self-expand in a manner such that the barrier device is placed between, and provides a structural barrier separating adjacent spinal cord nerves and the external compression at the external compression site;

(g) prior to step (d) performing the steps of:

1) advancing a wire of a shape memory material having a loop at a distal end thereof through the lumen of the delivery catheter;

2) extending the loop beyond the distal end of the delivery catheter and about a protuberance on a posterior surface of a vertebral body; and 3) advancing the distal end of the delivery catheter cephalically while holding the wire stationary to thereby close the loop about the protuberance to sever the protuberance.

4. The method of claim 3 and including a further step of aspirating the severed protuberance through the lumen of the delivery catheter.

5. The method of claim 1 wherein the delivery catheter includes radio-opaque markings at a distal end and at a predetermined distance proximal to the distal end.

6. The method of claim 3 wherein the delivery catheter includes radio-opaque markings at a distal end and at a predetermined distance proximal to the distal end.

7. The method of claim 1 wherein the pushing tool include a radio-opaque marking at a distal end thereof.

8. The method of claim 3 wherein the pushing tool include a radio-opaque marking at a distal end thereof.

9. The method of claim 1 wherein the delivery catheter comprises a plastic, flexible tube with a stiffened portion proximate a proximal end thereof.

10. The method of claim 3 wherein the delivery catheter comprises a plastic, flexible tube with a stiffened portion proximate a proximal end thereof.

11. The method of claim 1 wherein the pushing tool comprises a flexible, elongate wire.

12. The method of claim 3 wherein the pushing tool comprises a flexible, elongate wire.

* * * * *